United States Patent [19]

Lunn et al.

[11] 4,336,253
[45] Jun. 22, 1982

[54] CEPHALOSPORIN ANTIBIOTICS

[75] Inventors: William H. W. Lunn; John K. Shadle, both of Indianapolis, Ind.

[73] Assignee: Eli Lilly and Company, Indianapolis, Ind.

[21] Appl. No.: 242,792

[22] Filed: Mar. 11, 1981

[51] Int. Cl.$^3$ ............................................ C07D 501/38
[52] U.S. Cl. ...................................... 424/246; 544/25; 544/21
[58] Field of Search ............................ 544/27, 25, 26; 424/270

[56] References Cited

U.S. PATENT DOCUMENTS

| | | | |
|---|---|---|---|
| 3,792,047 | 2/1974 | Arkley et al. | 260/243 C |
| 4,152,432 | 5/1979 | Heymes et al. | 424/246 |
| 4,237,128 | 12/1980 | Cimarusti et al. | 424/246 |
| 4,258,041 | 3/1981 | O'Callaghan et al. | 424/246 |
| 4,264,595 | 4/1981 | Numata et al. | 544/25 |
| 4,278,671 | 2/1981 | Ochiai et al. | 544/25 |

FOREIGN PATENT DOCUMENTS

| | | |
|---|---|---|
| 853545 | 10/1977 | Belgium . |
| 2025398 | 1/1980 | United Kingdom . |
| 2027692 | 2/1980 | United Kingdom . |
| 2043641 | 10/1980 | United Kingdom . |

Primary Examiner—Nicholas S. Rizzo
Attorney, Agent, or Firm—William B. Scanlon; Arthur R. Whale

[57] ABSTRACT

Cephalosporin antibiotics represented by the formula

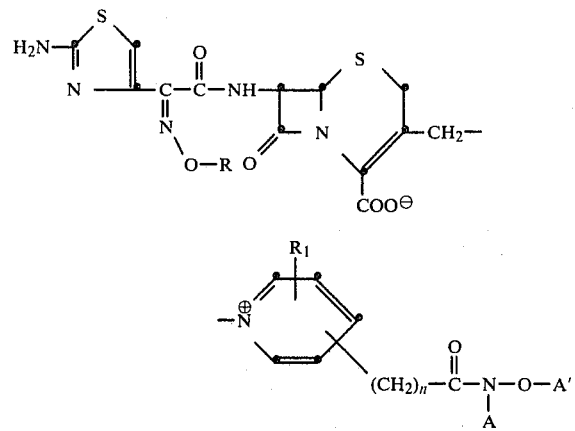

wherein R is hydrogen, $C_1$–$C_4$ alkyl or a carboxy substituted alkyl group; $R_1$ is H or $C_1$–$C_4$ alkyl; n is 0, 1 or 2; and A and A' independently are hydrogen, $C_1$–$C_4$ alkyl or allyl; and pharmaceutically acceptable salts thereof are broad spectrum antibiotics useful in the treatment of gram positive and gram negative infections of mammals.

30 Claims, No Drawings

CEPHALOSPORIN ANTIBIOTICS

BACKGROUND OF THE INVENTION

Among the earliest semi-synthetic cephalosporins discovered were the so-called cephalosporin $C_A$ (pyridine) type compounds which have a pyridinium or substituted pyridinium group at the 3' position of the cephem ring structure. The first pyridinium substituted cephalosporin was discovered by E. P. Abraham shortly after his discovery of cephalosporin C itself. See E. P. Abraham, et al., U.S. Pat. No. 3,226,384. The first and only cephalosporin $C_A$ derivative to find clinical use was cephalosporine, E. H. Flynn, U.S. Pat. No. 3,449,338. Spencer reviewed the earlier cephalosporin $C_A$ type compounds, J. L. Spencer, et al., "Chemistry of Cephalosporin Antibiotics VIII. Synthesis and Structure-Activity Relationships of Cephaloridine Analogues," Antimicrobial Agents and Chemotherapy-1966, pp. 573–580.

Recently, Heymes, et al., U.S. Pat. No. 4,152,432 describe cephalosporin antibiotics having a 7-(2-aminothiazol-4-yl)-2-oximinoacetamido side chain with the traditional acetoxymethyl group in the 3-position. These compounds are reported to be potent parenteral antibiotics. More recently $C_A$ (pyridine) compounds have been prepared which have the same 2-aminothiazole oxime substituted side chain. O'Callaghan, et al., U.K. patent application No. 2,025,398A describe such compounds having the pyridinium or a 3- or 4-carbamoylpyridinium group in the 3-position, while the oxygen atom of the α-oximino group is substituted with a $-C(CH_3)_2COOH$ group. Belgium Patent Specification No. 853,545 teaches certain 2-aminothiazole methoxyimino compounds substituted in the 3-position by pyridinium and substituted pyridinium.

SUMMARY OF THE INVENTION

Cephalosporin compounds substituted in the 3'-position with a pyridiniumhydroxamic acid group or a derivative thereof, and in the 7-position with 2-(2-aminothiazol-4-yl)-2-alkoxyiminoacetamido group are broad spectrum antibiotics provided by this invention. The 4-pyridinehydroxamic acid derivative represented by the following general formula

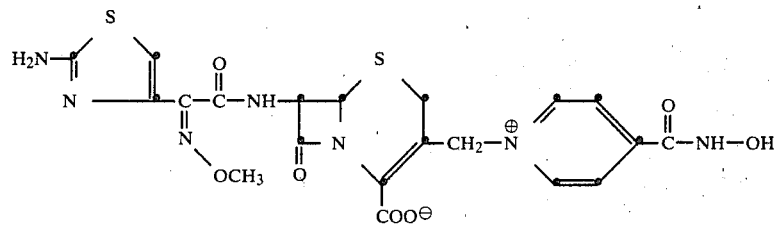

is an example.

The cephalosporin antibiotics of this invention are best prepared by reacting 7-[2-(2-aminothiazol-4-yl)-2-alkoxyiminoacetamido]-3-iodomethyl-3-cephem-4-carboxylic acid in the form of a silyl ester, for example the trimethylsilyl ester, with the pyridinehydroxamic acid or a derivative thereof. Alternatively, the cephalosporins of the invention are prepared with the corresponding 3-acetoxymethyl-3-cephem-4-carboxylic acid and the pyridinehydroxamic acid under anhydrous displacement conditions.

The pyridiniumhydroxamic acid substituted cephalosporins and derivatives thereof are useful in combatting infections in man and animals when administered parenterally in suitable formulations.

DETAILED DESCRIPTION OF THE INVENTION

The cephalosporin antibiotics of this invention are represented by the following structural formula 1.

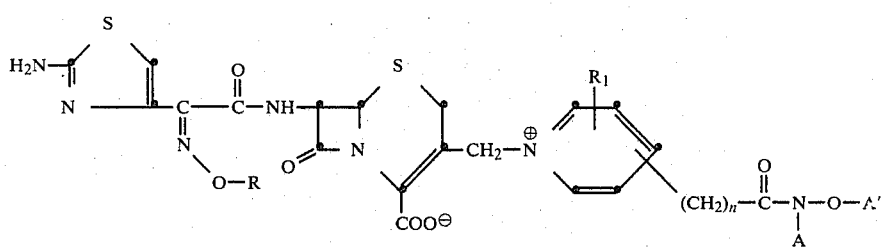

wherein R is hydrogen, $C_1$–$C_4$ alkyl or a group of the formula

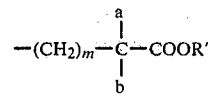

wherein m is 0, 1 or 2;

a and b independently are hydrogen or $C_1$–$C_3$ alkyl; or a and b when taken together with the carbon atom to which they are attached form a 3–6 membered carboxylic ring, and R' is hydrogen or a carboxy protecting group;

$R_1$ is hydrogen or $C_1$–$C_4$ alkyl;

n is 0 or an integer from 1 to 3;

A and A' independently are hydrogen, allyl, or $C_1$–$C_4$ alkyl; and the pharmaceutically acceptable, non-toxic salts thereof.

In the above description of the compounds provided by this invention, the term "$C_1$–$C_4$ alkyl" refers to methyl, ethyl, n-propyl, iso-propyl, n-butyl, sec-butyl, iso-butyl and t-butyl; "$C_1$–$C_3$ alkyl" refers to methyl, ethyl, n-propyl and iso-propyl; and "3–6 membered carboxylic ring" refers to cyclopropyl, cyclobutyl, cyclopentyl and cyclohexyl.

Illustrative of the R groups represented by

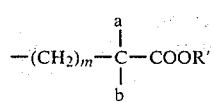

are 2-carboxy-2-propyl, 2-carboxy-2-butyl, 3-carboxy-3-pentyl, carboxymethyl, carboxyethyl, 1-carboxy-3-propyl, 1-carboxycycloprop-1-yl, 1-carboxycyclobut-1-yl, 1-carboxycyclopent-1-yl, and like carboxy substituted alkyl, branched alkyl and cycloalkyl groups.

The cephalosporin compounds of the invention are characterized by a substituted pyridinium group in the 3'-position wherein the substituent group on the pyridinium ring is an hydroxamic acid function, an alkylhydroxamic acid function, or an allyl or lower alkyl derivative thereof. Examples of such groups defined above for formula 1 are N-hydroxy 4-pyridinium carboxamide of the formula

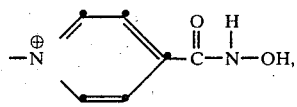

N-hydroxy 3-pyridiniumcarboxamide of the formula

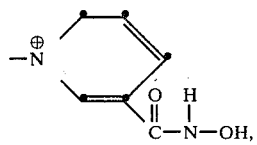

N-hydroxy 3-pyridiniumacetamide of the formula

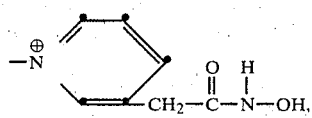

N-hydroxy 4-pyridiniumpropionamide of the formula

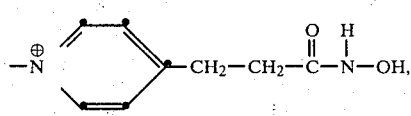

N-hydroxy 2-pyridiniumacetamide of the formula

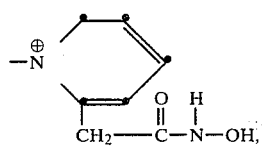

N-hydroxy-N-methyl 3-pyridiniumcarboxyamide of the formula

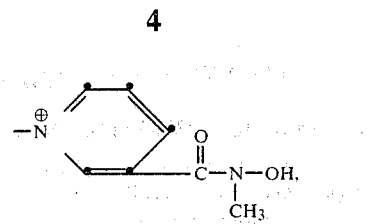

N-methoxy 4-pyridiniumacetamide of the formula

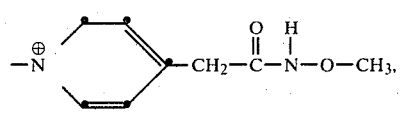

N-hydroxy-N-(n-propyl) 2-pyridiniumcarboxamide of the formula

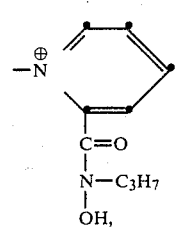

N-hydroxy-N-allyl 4-pyridiniumcarboxamide of the formula

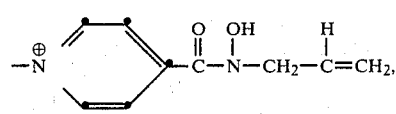

N-allyloxy-N-methyl 3-pyridiniumacetamide of the formula

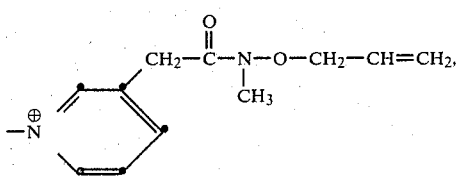

and N-hydroxy 4-pyridiniumbutyramide of the formula

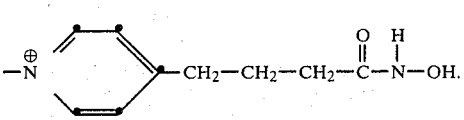

The compounds of the invention are also characterized by an oxime function in the 7-position side chain. The oxime group can exist in two isomeric (geometric) forms—the syn and anti forms. The compounds of the formula 1 are shown with the oxime function in the preferred syn-form. The syn-oximino compounds are preferred because of their higher antibiotic activity.

The 7-position side chain has the natural or β-configuration as do the cephalosporin antibiotics in general. In this configuration the 7-position side chain is located above the plane of the β-lactam ring while both of the hydrogens at $C_6$ and $C_7$ of the β-lactam ring are α- and therefore cis- to one another.

The 2-aminothiazole ring of the 7-position side chain can also exist in the tautomeric 2-imino form as shown below.

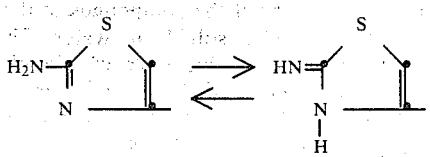

Although the structural formula 1 depicts the compounds of the invention as the 2-amino tautomers, it is to be understood that the tautomeric 2-imino form is encompassed as well.

The compounds of the invention are prepared with 7-[2-(2-aminothiazol-4-yl)-2-R-oximinoacetamido]-3-acetoxymethyl-3-cephem-4-carboxylic acid represented by the formula 2

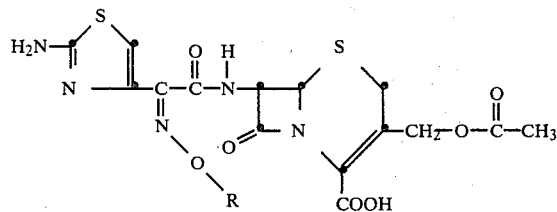

wherein R is as defined for formula 1. These 2-aminothiazol oximinocephalosporanic acids are known compounds, eg. Heymes, et al., U.S. Pat. No. 4,152,432, describe the above starting materials wherein R is $C_1$–$C_4$ alkyl, while O'Callaghan, et al., in U.K. patent application Nos. 2,025,398A and 2,027,692A describe the above starting materials wherein R is a carboxy substituted alkyl group or a carboxy-substituted cycloalkyl group.

According to a preferred method for preparing the compounds of the invention, a compound of the formula 2

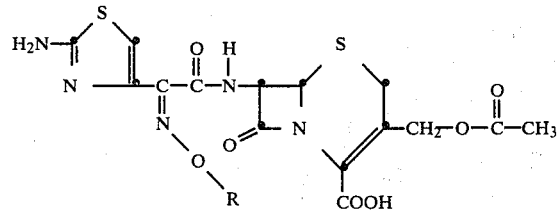

is first converted to the corresponding 3-iodomethyl derivative with trimethylsilyl iodide and the latter is reacted with the desired pyridinehydroxamic acid or silylated derivative thereof to form a compound of the formula 1. The preparation of the 3-iodomethylcephalosporin is carried out conveniently by the method of Bonjouklian as described in U.S. Pat. No. 4,266,049, issued May 5, 1981. According to this method, the compound of the formula 2 is first reacted under anhydrous conditions with a silylating agent to form the silyl derivative of the $C_4$ carboxylic acid group and the carboxy group of the oximino function, when present, as well as the amino function in the 2-position of the thiazole ring. The silylated derivative is represented by the following formula 3.

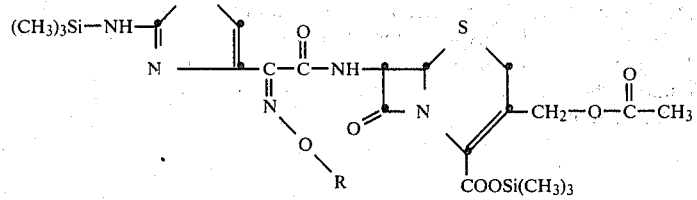

In the above formula the trimethylsilyl group is illustrative and preferred among the silyl groups which can be used. As noted above, when R is a carboxy substituted alkyl or cycloalkyl group, the trialkylsilyl ester derivative thereof is also formed. The function of silylation is to block the amino and carboxy groups from reaction with the trimethylsilyl iodide used in the method for preparing the 3-iodomethyl derivative.

A number of commonly used silylating agents can be used to form the compound of formula 2. Examples of such silylating agents are trimethylsilylacetamide, bis-trimethylsilylacetamide, trimethylsilylsuccinimide, bis-trimethylsilyltrifluoroacetamide, and the like.

The silyl protected derivative is then treated under anhydrous conditions in an inert solvent with trimethylsilyl iodide to form a trimethylsilyl iodide complex of the 3-iodomethyl compound represented by the formula 4.

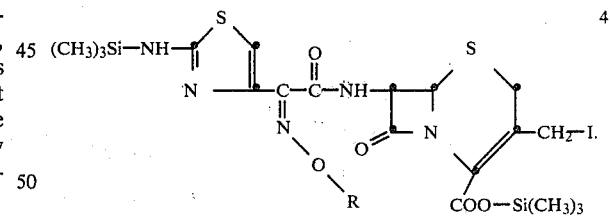

The reaction with the trimethylsilyl iodide is carried out at a temperature between about −5° C. and about 25° C. in an inert solvent. Suitable solvents are the chlorinated hydrocarbons such as methylene chloride, chloroform, dichloroethane, trichloroethane and the like, and lower alkyl nitriles such as acetonitrile and propionitrile. An amount of trimethylsilyl iodide in excess of one molar equivalent is used and, preferably, a hydrogen iodide scavenger such as amylene or butylene is used to trap hydrogen iodide which may be generated in the reaction mixture. The use of a hydrogen iodide scavenger is not essential, however, it aids in the isolation and purification of the final product.

The 3-iodomethyl silylated derivative is isolated simply by evaporation of the reaction mixture. The 3-iodomethyl product is then dissolved in a suitable organic aprotic solvent and is reacted with the desired silylated pyridinehydroxamic acid to form, following hydrolysis of the silyl protecting groups, a compound of the invention.

Aprotic solvents suitable in the reaction of the 3-iodomethylcephalosporin with the pyridinehydroxamic acid are acetonitrile, propionitrile, tetrahydrofuran, dioxane, dimethylformamide, dimethylacetamide, and like aprotic solvents.

When in the formula 1, A' is hydrogen the pyridinehydroxamic acid is preferably silylated prior to the reaction to prevent the occurrence of side reactions by the hydroxamic acid group. An excess of the molar equivalent amount of pyridinehydroxamic acid is desirably employed in the displacement reaction.

The above-described method for preparing the compounds of the invention is illustrated by the following reaction scheme.

The desilylation of the reaction product is accomplished by mild hydrolysis. For example, following the displacement reaction of the 3-iodomethyl cephalosporin with the pyridinehydroxamic acid, the reaction mixture is treated with a small amount of water or with a dilute solution of sodium bicarbonate. Because of the polar betaine structure of the compounds of the invention they are somewhat soluble in water. The compounds are generally insoluble in the aprotic solvents in which they are formed and the polar betaine product generally precipitates. Following filtration the compounds can be purified by trituration or extraction with water followed by chromatography of the material from the aqueous triturates or extracts with Sephadex G-10 (Pharmacia Fine Chemicals, Inc.), or other suitable polysaccharide dextran material.

The compounds of the invention can also be prepared by displacement of the acetoxy group of the 3-acetox-

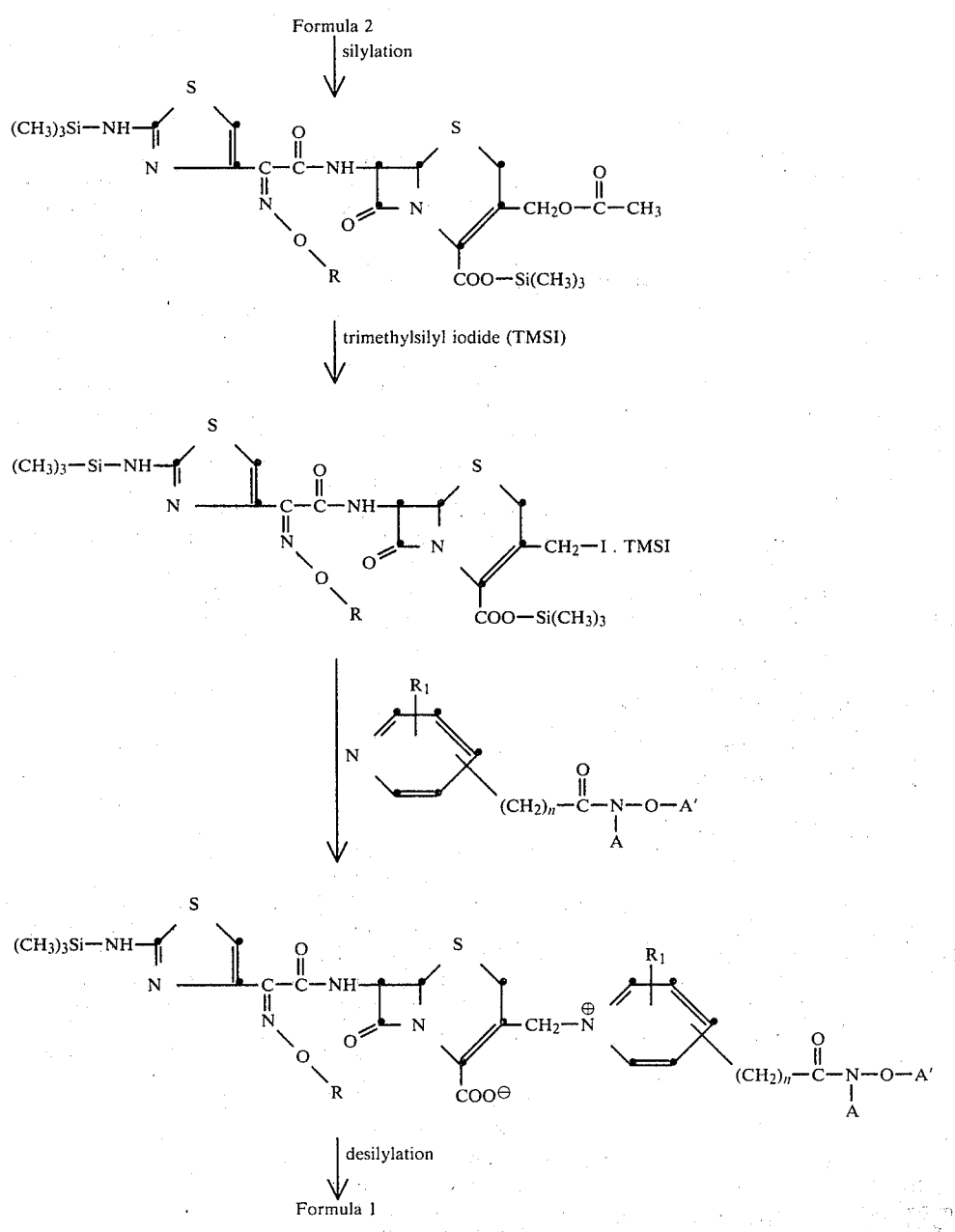

ymethyl-3-cephem starting material (formula 2) with the desired pyridinehydroxamic acid or derivative thereof. The displacement reaction is carried out by well known procedures for the preparation of cephalosporin C$_A$ type compounds. Preferably the displacement is carried out under non-aqueous conditions in a polar aprotic organic solvent such as dimethylacetamide, dimethylsulfoxide or dimethylformamide.

The 7-[2-(2-aminothiazol-4-yl)-2-hydroxyiminoacetamido]-3-acetoxymethyl-3-cephem-4-carboxylic acid which is used to prepare compounds of the formula 1 wherein R is hydrogen is obtained by the acylation of 7-aminocephalosporanic acid with the syn or anti isomer of the amino-protected acid.

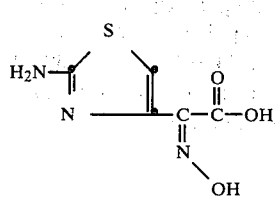

The acylation can be carried out using a coupling agent such as dicyclohexyldiimide or, alternatively, the acylation can be accomplished by using an active ester derivative of the acid. The active ester of hydroxybenzotriazole, HBT, is one such useful active ester.

The formation of the silylated 7-[2-(2-aminothiazol-4-yl)-2-hydroxyiminoacetamido]-3-iodomethyl-3-cephem-4-carboxylic acid, which is a precursor of the formula 1 compounds is carried out as described above for compounds of the formula 1 wherein R is other than hydrogen. The hydroxy group of the hydroxyimino substituent is silylated along with the C-4 carboxy group and the 2-amino group of the thiazole ring.

The preferred compounds of the formula 1 wherein the oximino group is syn are prepared with the syn isomer of the 2-(2-aminothiazol-4-yl)-2-oximinoacetic acid while the anti isomer is prepared with the anti-oximino acid. The preparation of these acids is known in the art, for example, as taught by Heymes, et al., U.S. Pat. No. 4,196,205.

The pyridinehydroxamic acids and the derivatives thereof are prepared with an ester of the corresponding pyridine carboxylic acid and the hydroxylamine or the substituted hyroxylamine as illustrated in the following reaction scheme.

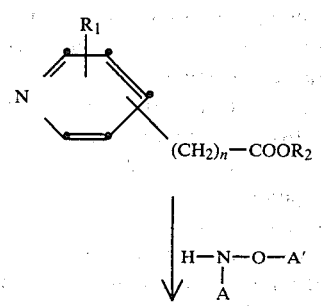

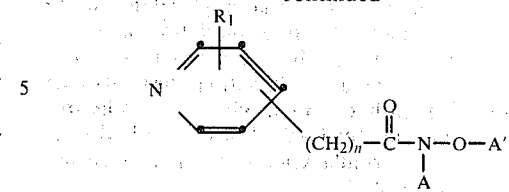

wherein R$_1$, A, and A' have the same meanings as defined for formula 1, and R$_2$ is the residue of an ester group such as a lower alkyl group, eg. a methyl or ethyl group.

The reaction of the hydroxylamine with the pyridine ester is carried out conveniently in a lower alkyl alcohol such as methyl alcohol or ethyl alcohol at about room temperature. The reaction proceeds best when a molar equivalent of an alkali metal alkoxide is used. Alkali metal lower alkoxides such as sodium methylate and sodium ethylate are preferable. Sodium methylate is readily available and is the preferred alkoxide.

In general, the preparation of the pyridine hydroxamic acids and derivatives thereof is carried out by adding one molar equivalent of the pyridine ester to a solution of the hydroxylamine or substituted hydroxylamine in methyl alcohol. After the mixture is stirred at about room temperature, one molar equivalent of sodium methylate is added and the mixture is stirred until the reaction is complete.

The hydroxylamines used in the preparation are usually obtained as salts such as the hydrochloride salts. For example, hydroxylamine hydrochloride and methoxyamine hydrochloride are commercially available salts. Prior to use in the preparation of the pyridinehydroxamic acids the hydroxylamine is liberated from the salt form with a suitable base such as triethylamine. The free base form is conveniently generated by adding one equivalent of triethylamine to a solution of the hydroxylamine salt in methyl alcohol. This solution of the free base form of the hydroxylamine is then used in the preparation of the pyridinehydroxamic acid as described above. Alternatively, the free base form of the hydroxylamine can be generated in the solvent with the sodium methylate employed in the condensation with the pyridine ester. In this instance, at least two molar equivalents of sodium methylate are used; one equivalent for springing the hydroxylamine from its salt, and one equivalent for the reaction of the hydroxylamine with the pyridine ester.

The O-alkyl and O-allyl derivatives of the hydroxylamine represented by the formula

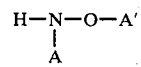

wherein A' is C$_1$–C$_4$ alkyl or allyl are prepared by alkylating an N-protected derivative of the hydroxylamine with an alkyl halide or allyl halide with a base. The amino group can be protected by oxime formation, for example by condensation of the hydroxylamine with a dialkyl ketone such as acetone or with an aromatic aldehyde such as benzaldehyde or a substituted benzaldehyde such as p-nitrobenzaldehyde. The oxime formation is carried out in a conventional manner by reacting hydroxylamine with the ketone or aldehyde. The oxime is then O-alkylated under anhydrous conditions with a strong base such as sodium methylate or sodium ethylate and a $C_1$–$C_4$ alkyl halide or an allyl halide. In the condensation, the more reactive alkyl bromides and iodides are best used while allyl chloride serves best as the allyl halide. Following the alkylation, the O-alkyl or O-allyl oxime is then hydrolyzed with aqueous hydrochloric acid to provide the O-alkyl or O-allyl hydroxylamine of the above formula wherein A is hydrogen and A' is $C_1$–$C_4$ alkyl or allyl.

The O-alkyl hydroxylamine is used to prepare the N-alkyl-(or N-allyl)-O-alkyl(or O-allyl) hydroxylamine where A and A' are other than hydrogen. The O-alkylhydroxylamine is reacted with a $C_1$–$C_4$ alkyl aldehyde to form the O-alkyloxime which is then hydrogenated over a suitable catalyst such as 5% Pd/C. For example, O-ethylhydroxylamine on reaction with acetaldehyde in ethyl alcohol in the presence of pyridine forms the O-ethyloxime. The latter is then hydrogenated at about 50 psi hydrogen pressure over 5% Pd/c in tetrahydrofuran, or other suitable solvent. The N,O-dialkylhydroxylamines can be isolated as salts, for example as the hydrochloride salt. The above reaction sequence is illustrated below wherein A and A' are ethyl.

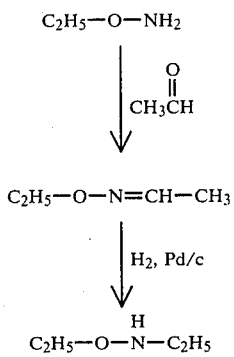

The O-allylhydroxylamines cannot be used in the above manner since the O-allyl group is reduced to the O-n-propyl group. The N,O-diallyl and N-alkyl-O-allylhydroxylamines are prepared by N-alkylation of the O-allylhydroxylamine with allyl chloride and a base such as potassium t-butoxide, sodium methylate or sodium hydride in an aprotic solvent such as acetonitrile, tetrahydrofuran or methylene chloride.

Hydroxylamines of the formula A-NH-OH wherein A is $C_1$–$C_4$ alkyl or allyl are prepared by O-alkylating an oxime with benzyl chloride and thereafter hydrolyzing the oxime to the O-benzylhydroxylamine (Behrend and Leuchs, Annalen, 257, 203 (1890). The O-benzyl derivative is then reacted with a $C_1$–$C_4$ alkyl aldehyde to form the O-benzyl oxime and the latter is catalytically reduced and debenzylated to the N-($C_1$–$C_4$ alkyl)-hydroxylamine.

The hydroxylamine hydroxy group also can be protected with other suitable hydroxy-protecting groups such as the trityl group or the tetrahydropyran group.

The O-protected hydroxylamine is N-alkylated with allyl chloride and the protecting group removed to provide N-allylhydroxylamine ($CH_2=CH-CH_2-NH-OH$).

Examples of the pyridine carboxylic acid esters which can be used to prepare the hydroxamic acids are methyl 4-pyridinecarboxylate, methyl 2-pyridinecarboxylate, methyl 3-pyridinecarboxylate, methyl 4-(3-methylpyridine)carboxylate, methyl 4-pyridineacetate, ethyl 3-pyridineacetate, methyl 4-pyridine propionate, ethyl 4-pyridinepropionate, benzyl 4-pyridinecarboxylate, methyl 4-(2-methylpyridine)-acetate, methyl 3-(4-methylpyridine)propionate, methyl 2-(4-methylpyridine)carboxylate and the like.

As was described hereinabove, the compounds of the invention are prepared with a compound of the formula 2. These starting materials wherein R is a group of the formula

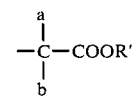

are prepared by known procedures such as those described for the preparation of the compounds described in U.K. patent application No. G.B. 2,025,398A and U.S. Pat. Nos. 4,144,392 and 4,144,393. For example, an amino-protected and esterified 2-aminothiazole oxime represented by the formula

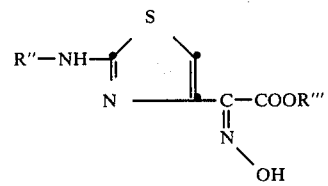

wherein R'' is an amino-protecting group and R''' is a carboxy-protecting group is O-alkylated with halo substituted alkyl or cycloalkyl carboxylic acid ester represented by the formula

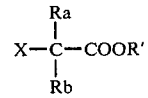

wherein X is chloro, bromo or iodo and Ra, Rb and R' is a carboxy-protecting ester moiety. The O-alkylation is carried out in an aprotic solvent such as tetrahydrofuran, acetonitrile, dimethylformamide or other suitable solvent in the presence of a base such as an alkali metal carbonate, potassium t-butoxide or sodium hydride. For example, p-methoxybenzyl 2-(2-tritylaminothiazol-4-yl)-2-oximinoacetate is reacted in dimethylformamide with one molar equivalent of sodium hydride and one molar equivalent of t-butyl 2-bromoisobutyrate to form p-methoxybenzyl 2-(2-tritylaminothiazol-4-yl)-2-(2-t-butyloxycarbonylprop-2-oxyimino)acetate. The p-methoxybenzyl ester is deesterified and the O-alkyl thiazoleacetic acid oxime is converted to an active ester. The latter is used to acylate 7-aminocephalosporanic acid. The hydroxybenzotriazole (HBT) ester is the preferred active ester used in the acylation of 7ACA to obtain a compound of the formula 2.

The preparation of the 2-aminothiazole oxime can be carried out also by reacting 2-aminothiazolglyoxylic acid with the desired O-alkylated hydroxylamine as illustrated by the following reaction scheme.

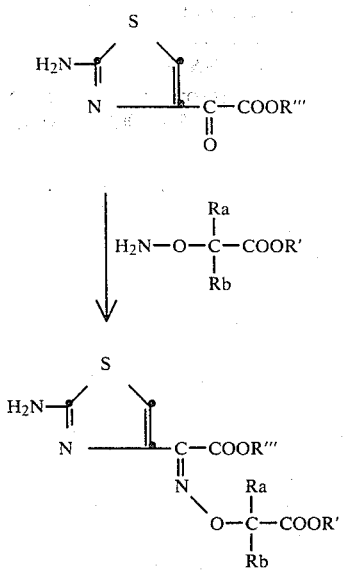

The above method is generally useful in the preparation of compounds of the formula 1 wherein Ra and Rb form a C3–C6 cycloalkyl ring.

The above-described procedures for the preparation of the compounds of the invention employ the carboxy-protecting groups represented by R' and R'''. Many suitable esters can be formed to achieve the desired protection. Such protecting ester groups are well known in the cephalosporin art and include the alkyl and substituted alkyl esters such as methoxymethyl, 2-iodoethyl, 2,2,2-trichloroethyl, and t-butyl; the arylmethyl and diarylmethyl esters such as benzyl, methylbenzyl, p-methoxybenzyl, p-nitrobenzyl, diphenylmethyl, p-methoxydiphenylmethyl, p,p'-dimethoxydiphenylmethyl, and like esters; and other esters such as phenacyl and phthalimidomethyl esters. Other esters which may find use are referred to by E. Haslam, *Protective Groups In Organic Chemistry*, Ch. 5, Ed., McOmie Plenum Press, New York 1973.

Exemplary compounds of the invention include the following:

syn-7-[2-(2-aminothiazol-4-yl)-2-methoxyiminoacetamido]-3-[[4-(N-hydroxycarbamoyl)-1-pyridinium]-methyl]-3-cephem-4-carboxylate, syn-7-[2-(2-aminothiazol-4-yl)-2-methoxyiminoacetamido]-3-[[3-(N-hydroxycarbamoyl)-1-pyridinium]-methyl]-3-cephem-4-carboxylate, syn-7-[2-(2-aminothiazol-4-yl)-2-ethoxyiminoacetamido]-3-[[3-(N-hydroxycarbamoyl)-1-pyridinium]-methyl]-3-cephem-4-carboxylate, syn-7-[2-(2-aminothiazol-4-yl)-2-t-butoxyiminoacetamido]-3-[[4-(N-hydroxycarbamoyl)-1-pyridinium]methyl]-3-cephem-4-carboxylate, syn-7-[2-(2-aminothiazol-4-yl)-2-(2-carboxyprop-2-oxyimino)acetamido]-3-[[4-(N-hydroxycarbamoyl)-1-pyridinium]methyl]-3-cephem-4-carboxylate, syn-7-[2-(2-aminothiazol-4-yl)-2-(1-carboxycyclobut-1-oxyimino)acetamido]-3-[[3-(N-methoxycarbamoyl)-1-pyridinium]methyl]-3-cephem-4-carboxylate, syn-7-[2-(2-aminothiazol-4-yl)-2-(1-carboxycyclopent-1-yloxyimino)acetamido]-3-[(N-hydroxy 3-pyridiniumacetamide)methyl]-3-cephem-4-carboxylate, syn-7-[2-(2-aminothiazol-4-yl)-2-(1-carboxycycloprop-1-yloxyimino)acetamido]-3-[(N-hydroxy 4-pyridiniumpropionamide)methyl]-3-cephem-4-carboxylate, syn-7-[2-(2-aminothiazol-4-yl)-2-(2-carboxyprop-1-yloxyimino)acetamido]-3-[(N-methoxy 4-pyridiniumbutyramido)methyl]-3-cephem-4-carboxylate, syn-7-[2-(2-aminothiazol-4-yl)-2-methoxyiminoacetamido]-3-[[3-(N-hydroxy-N-methylcarbamoyl)-1-pyridinium]methyl]-3-cephem-4-carboxylate, syn-7-[2-(2-aminothiazol-4-yl)-2-methoxyiminoacetamido]-3-[[4-(N-methoxy-N-butylcarbamoyl)-1-pyridinium]methyl]-3-cephem-4-carboxylate, syn-7-[2-(2-aminothiazol-4-yl)-2-isopropoxyiminoacetamido]-3-[[2-(N-hydroxy-N-allylcarbamoyl)-1-pyridinium]methyl]-3-cephem-4-carboxylate, syn-7-[2-(2-aminothiazol-4-yl)-2-t-butoxyiminoacetamido]-3-[(N-hydroxy-N-methyl 3-pyridiniumacetamide)methyl]-3-cephem-4-carboxylate, syn-7-[2-(2-aminothiazol-4-yl)-3-[[4-(N-allyl-N-allyloxycarbamoyl)-1-pyridinium]methyl]-3-cephem-4-carboxylate, syn-7-[2-(2-aminothiazol-4-yl)-2-hydroxyiminoacetamido]-3-[[3-(N-hydroxycarbamoyl)-1-pyridinium]methyl]-3-cephem-4-carboxylate, syn-7-[2-(2-aminothiazol-4-yl)-2-hydroxyimino]-3-[(N-hydroxy 3-pyridiniumacetamide)methyl]-3-cephem-4-carboxylate, and syn-7-[2-(2-aminothiazol-4-yl)-2-hydroxyimino]-3-[[4-(N-hydroxycarbamoyl)-1-pyridinium]methyl]-3-cephem-4-carboxylate.

A preferred group of compounds of the invention are represented by the formula 1 wherein R is a C1–C4 alkyl group and R1 is hydrogen. Especially preferred are compounds wherein R is methyl (the methoxyimino derivative), R1 is hydrogen and n, A and A' are as shown in the following table.

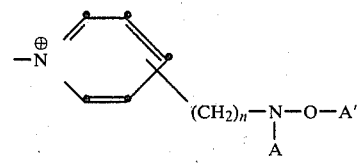

| n | A | A' | Isomer |
|---|---|---|---|
| 0 | H | H | 4 |
| 0 | H | H | 3 |
| 1 | H | H | 4 |
| 1 | H | H | 3 |
| 0 | CH3 | H | 4 |
| 0 | CH3 | H | 3 |
| 0 | H | CH3 | 4 |
| 0 | H | CH3 | 3 |
| 1 | H | CH3 | 3 |
| 1 | H | CH3 | 4 |

A further preferred group of compounds are represented by the formula 1 wherein R is —C(CH3)2—COOH and n, A and A' have the same meanings as shown in the above table and the substituent is located at either the 3- or 4-position of the pyridinium ring.

The compounds of the invention form salts with suitable bases, for example the alkali and alkaline metal, ammonium and amine salts such as the sodium, potassium, calcium, ammonium, dibenzylammonium, benzylammonium, 2-hydroxyethylammonium, bis(2- hydroxyethyl)ammonium, and like salts. Other amine salts can be formed with procaine and the amino acids such as the glycine and phenylglycine salts. These salts are useful in preparing suitable pharmaceutical formulations of the antibiotics for therapeutic purposes. Because of the basic amino group in the 2-position of the thiazole ring moiety, the compounds of the invention form acid addition salts with suitable acids such as hydrochloric acid, hydrobromic acid, phosphoric acid, sulfuric acid, the organic sulfonic acids, eg. methanesulfonic acid, benzenesulfonic acid, toluenesulfonic acid, and like acids. The acid addition salts also may be used for preparing suitable pharmaceutical formulations of the antibiotics.

The compounds of the invention inhibit the growth of microorganisms pathogenic to man and animals. They are broad spectrum antibiotics which control the growth of gram positive and gram negative bacteria, for example, *Staphylococcus aureus*, Streptococcus, Hemophilus influenzae, Shigella sp., *Escherichia coli*, Klebsiella sp., Enterobacter, Salmonella, Pseudomonas species, Serratia, Proteus species, and Citrobacter.

The cephalosporin compounds of the invention are useful in the treatment of infectious diseases in man and animals caused by gram positive and gram negative microorganisms. The compounds as the free acids, or a suitable salt form thereof, are administered parenterally, i.e., intravenously, intramuscularly, or subcutaneously in a non-toxic effective dose between about 25 mg/kg and about 500 mg/kg. The treatment regime may comprise a single daily dose or multiple daily doses, eg. three or four doses administered every 8 or 6 hours, respectively. The particular treatment regime is a clinical matter dependent upon such factors as the particular microorganism, the severity of the infection, the site of infection, and the age and general condition of the patient. The antibiotics of the invention may also be administered rectally in a suitable rectal formulation such as a suppository.

The compounds of the invention can be formulated for administration parenterally into suitable dosage unit forms. For example, for intravenous use the compound of the formula 1, preferably in salt form such as the sodium or potassium salt, can be made up in a suitable physiological fluid such as 5% dextrose, Ringer's solution, or physiological saline. For intramuscular injection the antibiotic, preferably in salt form, can be made up in unit dosage form in sterile ampoules as a dry powder which is reconstituted in Water for Injection or other suitable vehicle prior to use.

This invention also provides pharmaceutical compositions suitable for therapeutic use which comprise a compound of the formula 1 and a pharmaceutically acceptable carrier. Compositions containing between about 1% and about 95% of the antibiotic active ingredient and a pharmaceutically acceptable carrier are suitable for use in treatment. Dosage unit compositions may contain from about 0.5 mg. to about 2,000 mg per unit. Such compositions may contain excipients, emulsifying agents and stabilizing agents as well as the pharmaceutical diluent.

The compounds of the invention also can be prepared in suitable veterinary formulations for therapeutic use in animals such as cattle, horses, swine, sheep and poultry, for example, chickens.

This invention is further illustrated and exemplified by the following Examples.

Abbreviations used in the Examples are as follows: DMF=dimethylformamide; BSTFA=bistrimethylsilyltrifluoroacetamide; HPLC=high performance liquid chromatography; TMSI=trimethylsilyl iodide.

Nuclear magnetic resonance spectra (NMR) were run on a Joel model No. FX-90Q, 90 MHz spectrometer.

EXAMPLE 1 syn-7-[2-(2-Aminothiazol-4-yl)-2-methoxyiminoacetamido]-3-[[4-(N-hydroxycarbamoyl)-pyridinium]methyl]-3-cephem-4-carboxylate A. Preparation of N-Hydroxy 4-pyridinecarboxamide A solution of 13.8 g. (200 mmole) of hydroxylamine hydrochloride and 27.8 ml. (200 mmole) of triethylamine in 500 ml. of methyl alcohol was formed and cooled to −5° C. To the cold solution were added with stirring 27.4 ml. (200 mmole) of methyl 4-pyridinecarboxylate and the mixture was allowed to warm to room temperature. After stirring for 5.5 hours, 10.8 g. (200 mmole) of sodium methylate were added. The reaction mixture was then stirred for 27.5 hours and was filtered. The filtrate was evaporated to dryness and the reaction product residue was sonicated with 50 ml. of chloroform to form a suspension. The suspension was filtered yielding 33.73 g. of crude product contaminated with salts. The crude product was crystallized from 50 ml. of water. There were obtained 9.5 g. of 4-pyridinehydroxamic acid melting with decomposition at about 163° C.

B. Preparation of Title Compound syn-7-[2-(2-Aminothiazol-4-yl)-2-methoxyiminoacetamido]-3-acetoxymethyl-3-cephem-4-carboxylic acid, 3.64 g. (8 mmole) and 3.12 ml. (12 mmole) of bistrimethylsilyltrifluoroacetamide were mixed with 30 ml. of methylene chloride and the mixture was heated to 40° C. for about two hours. The solution was cooled and 3.4 ml. of trimethylsilyl iodide were added. The mixture was stirred at room temperature for 1.5 hours and was then evaporated to remove the solvent and volatiles. To the residue were added 40 ml. of hexane and 40 ml. of acetonitrile. One-fourth of the mixture was added to a solution of 414 mg. (3 mmole) of 4-pyridinehydroxamic acid and 3 mmole of BSTFA in 5 ml. of acetonitrile and the reaction mixture was stirred at room temperature for 2 hours. Water, 0.4 ml., was added to the mixture and the precipitate filtered to provide 1.07 g. of crude product. The crude material was triturated three times with 1 ml. portions of water. Each triturate was filtered. The first two filtrates were combined and chromatographed over 25 g. of Sephadex. Three fractions labeled C (25 mg), D (40 mg), and E (180 mg) were obtained. The D fraction was again chromatographed over 25 g. of Sephadex G-10 yielding G (23 mg) and H (18 mg). The nmr spectra of the fractions demonstrated that fractions C, G, and H were the desired product.

NMR (DMSO): signals at 3.51 (q), 3.82 (s, 3H), 5.23 (d, 1H), 5.62 (q, 2H), 5.72 (s, 1H), 6.26 (broad, 2H, exch.), 8.46 (d, 2H), 9.21 (d, 2H), and 9.68 (d, 1H, exch.)δ.

EXAMPLE 2 syn-7-[2-(2-Aminothiazol-4-yl)-2-methoxyiminoacetamido]-3-[(N-hydroxy-3-pyridiniumacetamide)methyl]-3-cephem-4-carboxylate A. Preparation of N-hydroxy 3-pyridineacetamide A solution of 13.8 g. (200 mmole) of hydroxylamine hydrochloride and 27.8 ml. (200 mmole) of triethylamine in 500 ml. of methyl alcohol was cooled to a temperature of −5° C. and 30.2 g. (200 mmole) of methyl 3-pyridineacetate were added. The mixture was stirred for 6 hours at room temperature and then 10.8 g. (200 mmole) of sodium methylate were added causing a slight exotherm to occur. The reaction mixture was then stirred for 27.5 hours. The reaction mixture was filtered and the filtrate evaporated to dryness. The crude residue of product was sonicated with 50 ml. of chloroform and filtered. The insoluble crude product (25.10 g) was crystallized from 50 ml. of water. There were obtained 15.54 g. of product melting with decomposition at about 163° C. to about 165° C.

Elemental analysis calculated for $C_7H_8N_2O_2$: Theory: C, 55.26; H, 5.30; N, 18.41; O, 21.03. Found: C, 55.03; H, 5.09; N, 18.16; O, 20.86.

The product on electrometric titration in water showed two titratable groups at pKa 4.60 and 9.09, while in 66% DMF two titratable groups at 3.68 and 11.49.

B. Preparation of Title Compound

A solution of approximately 0.91 g. (2 mmole) of syn-7-[2-(2-aminothiazole-4-yl)-2-methoxyiminoacetamido]-3-iodomethyl-3-cephem-4-carboxylic acid trimethylsilyl ester in about 10 ml. of acetonitrile was added to a solution of 456 mg. (3 mmole) of N-hydroxy-3-pyridineacetamide and 3 mmole of bis-trimethylsilyltrifluoroacetamide in 5 ml. of acetonitrile and the mixture stirred for 1.5 hours at room temperature. After stirring, 0.4 ml. of water was added and mixture filtered. The crude reaction product which precipitated was triturated three times with 1 ml of water each time. Each triturate was filtered and the filtrates combined and chromatographed over 120 g. of Sephadex G-10. There was obtained a 50 mg. fraction of the product and a 385 mg. fraction of less pure product.

NMR (DMSO): signals at 3.38 (q, 2H), 3.64 (s, 2H), 3.80 (s, 3H), 5.10 (d, 1H), 5.50 (q, 2H), 5.70 (q, 1H), 6.74 (s, 1H), 7.22 (broad, 2H, exch.), 8.19 (t, 1H), 8.55 (d, 1H), 9.44 (d, 2H), and 9.58 (d, 2H, exch.) δ.

EXAMPLE 3 syn-7-[2-(2-Aminothiazol-4-yl)-2-methoxyimino]-3-[(N-hydroxy-2-pyridiniumacetamido)methyl]-3-cephem-4-carboxylate A. Preparation of N-hydroxy-2-pyridineacetamide A solution of 13.8 g. (200 mmole) of hydroxylamine hydrochloride and 27.8 ml. (200 mmole) of triethylamine in 500 ml. of methyl alcohol was cooled to −5° C. and 27.0 ml. (200 mmole) of methyl 2-pyridineacetate were added. The mixture was stirred at room temperature for 6 hours. Then 10.8 g. (200 mmole) of sodium methylate were added and stirring was continued for 27.5 hours. The reaction mixture was filtered to remove insolubles and the filtrate evaporated to dryness. The crude reaction product residue was sonicated with 50 ml. of chloroform and filtered. The insoluble crude product, 24.37 g., was crystallized from 50 ml. of water. There were obtained 14.86 g. of the crystalline product melting with decomposition at about 157° C. to about 161° C.

Elemental analysis calculated for $C_7H_8N_2O_2$: Theory: C, 55.26; H, 5.30; N, 18.41. Found: C, 54.81; H, 5.16; N, 18.05.

Electrometric titration:

water—pKa=4.05, 9.20
66% DMF—ca 3.4, 11.68

B. Preparation of Title Compound

To a suspension of 910 mg. (2 mmole) of syn-7-[2-(2-aminothiazole-4-yl)-2-methoxyimino]-3-acetoxymethyl-3-cephem-4-carboxylic acid in 10 ml. of methylene chloride were added 270 μl (1 mmole) of bis-trimethylsilyltrifluoroacetamide and the mixture was heated for 2 hours at 40° C. to obtain a complete solution. The solution was cooled to room temperature and 850 μl of trimethylsilyl iodide were added. The reaction mixture was stirred for 1.5 hours and was then evaporated to dryness under vacuum. The residue of the 3-iodomethyl intermediate was dissolved in 10 ml. of acetonitrile and the solution washed with 10 ml. of hexane.

The acetonitrile solution of the 3-iodomethyl cephalosporin intermediate was added to a solution of 456 mg. (3 mmole) of N-hydroxy-2-pyridineacetamide and 3 mmole of BSTFA in 5 ml. of acetonitrile. After the reaction mixture was stirred for 2 hours, 0.4 ml. of water were added and the insoluble product was filtered. The product, 1.25 g., was extracted three times with a 1 ml. portion of water and each extract was filtered. The three extracts were combined and passed over 120 g. of Sephadex G-10. There were obtained 25 mg. of the product cephalosporin.

NMR (DMSO): signals at 3.48 (q, 2H), 3.80 (s, 2H), 3.86 (s, 3H), 5.14 (d, 1H), 5.36 (q, 2H), 5.78 (q, 1H), 6.82 (s, 1H), 7.24 (broad, 2H, exch.), 7.75 (d, 1H), 8.02 (m, 1H), 8.48 (d, 1H), 9.07 (m, 1H), and 9.65 (d, 1H, exch.) δ.

EXAMPLE 4 syn-7-[2-(2-Aminothiazol-4-yl)-2-methoxyiminoacetamido]3-[[3'-(N-hydroxycarbamoyl)-pyridinium]methyl]-3-cephem-4-carboxylate A. Preparation of N-hydroxy-3-pyridinecarboxamide A solution of 21.06 g. (0.39 mole) of sodium methylate in 60 ml. of methyl alcohol was obtained at 70° C., cooled to 40° C. after the solution formed and was mixed at 40° C. with a solution of 18.08 g. (0.26 mole) of hydroxylamine hydrochloride in 90 ml. of methyl alcohol. The solution was cooled to 5° C. and a solution of 20 g. (0.13 mole) of ethyl nicotinate in 50 ml. of methyl alcohol was added to the cold solution by dropwise addition. The reaction mixture was stirred and allowed to warm to room temperature. The mixture was filtered, the filtrate concentrated and diluted with 1750 ml. of ether and refiltered. The insoluble product was dissolved in 50 ml. of hot 1.25 N acetic acid, filtered while hot, and the filtrate cooled to room temperature and the product crystallized. The insoluble precipitate from the hot acetic acid crystallization was slurried in 50 ml. of methyl alcohol and filtered. The filtrate was evaporated to dryness in vacuo and the residue of product crystallized from hot 1.25 N acetic acid.

Both samples of crystalline product obtained from hot acetic acid were combined for a total weight of 6.21 g. (35% yield) of product.

The product on electrometric titration showed the following pKa in the indicated solvent.

| Solvent | pKa |
| --- | --- |
| 50% methyl alcohol | 2.60 and 9.0 |
| 66% DMF | ca 2.5 and 9.90 |

| Solvent | pKa |
| --- | --- |
| water | 3.09 and 8.29 |

B. Preparation of Title Compound

A solution of 3 mmole of trimethylsilylated syn-7-[2-(2-aminothiazol-4-yl)-2-methoxyiminoacetamido]-3-iodomethyl-3-cephem-4-carboxylic acid in acetonitrile was added to a solution of 415 mg. (3 mmole) of N-hydroxy 3-pyridinecarboxamide in 5 ml. of acetonitrile containing 800 μl (3 mmole) of BSTFA. The reaction mixture was stirred for 2 hours at room temperature and then was treated with 0.4 ml. of water. The reaction mixture was filtered to provide 1.025 g. of crude product. The product was triurate 3 times with 1 ml. of water each and the triturate filtered each time. The filtrates were combined and run over 125 g. of Sephadex G-10. There were obtained 45 mg. of the title compound.

NMR (DMSO): signals at 3.38 (q, 2H), 3.82 (s, 3H), 4.14 (d, 1H), ca. 4.5 (broad q, 2H), 5.74 (q, 1H), 6.75 (s, 1H), 7.22 (broad, 2H, exch.), 8.33 (m, 1H), 8.88 (d, 1H), 9.52 (m, 2H), and 9.68 (d, 1H, exch.) δ.

EXAMPLE 5 syn-7-[2-(2-Aminothiazol-4-yl)-2-methoxyiminoacetamido]3-[(N-hydroxy-4-pyridiniumacetamide)methyl]-3-cephem-4-carboxylate

A. Preparation of N-hydroxy 4-pyridineacetamide

To a suspension of 25.0 g. (157 mmoles) of 4-pyridineacetic acid hydrochloride in 50 ml. of DMF were added in portions 25.5 g. (157 mmoles) of N,N'-carbonyldiimidazole until a complete solution was obtained. Next were added 11.2 g. (160 mmole) of hydroxylamine hydrochloride and the reaction mixture was stirred for 45 minutes. The reaction mixture was evaporated to dryness under vacuum and the residue shaken with 100 ml. of water. The insoluble product, N-hydroxy 4-pyridineacetamide, was filtered and dried. There were obtained 5.8 g. of the product melting at about 178° C. to about 180° C. with decomposition.

Elemental analysis calculated for $C_7H_8N_2O_2$: Theory: C, 55.26; H, 5.30; N, 18.41; O, 21.03. Found: C, 55.11; H, 5.36; N, 18.14; O, 21.33.

B. Preparation of Title Compound

A solution of about 2 mmole of silylated syn-7-[2-(2-aminothiazol-4-yl)-2-methoxyiminoacetamido]-3-iodomethyl-3-cephem-4-carboxylic acid in 8 ml. of acetonitrile was added to a solution of 455 mg. (3 mmole) of the N-hydroxy 4-pyridineacetamide (Part A) and 800 μl. of BSTFA in 5 ml. of acetonitrile and the reaction mixture was stirred at room temperature for one hour. The reaction mixture was treated with 0.4 ml. of water and the impure product filtered. There were obtained 1.03 g. of the crude product. The product was triturated three times with a 1 ml. portion of water each time. The aqueous phase was separated from the solid phase after each trituration and the aqueous phase of the first two triturations was combined and passed over 125 g. of Sephadex G-10. There were obtained 25 mg. of the product.

NMR (DMSO): signal at 3.42 (q, 2H), 3.50 (s, 2H), 3.84 (s, 3H), 5.15 (d, 1H), 5.42 (q, 2H), 5.73 (q, 1H), 6.76 (s, 1H), 8.13 (d, 2H), 9.10 (d, 2H), 9.62 (d, 1H), and 7.24 (broad, 2H, exch.) δ.

EXAMPLE 6 syn-7-[2-(2-Aminothiazol-4-yl)-2-methoxyiminoacetamido]3-[[2-(N-hydroxycarbamoyl)pyridinium]methyl]-3-cephem4-carboxylate

A. Preparation of N-hydroxy 2-pyridinecarboxamide

To a suspension of 25.4 g. (365 mmole) of hydroxylamine hydrochloride in one liter of methyl alcohol were added 39.4 g. (730 mmole) of sodium methylate. A slight exotherm occurred and sodium chloride precipitated. The solution was allowed to cool to room temperature, 50 ml. (365 mmole) of methyl 2-pyridinecarboxylate were added, and the reaction mixture was stirred overnight. The mixture was filtered to remove the salt precipitate and the filtrate was evaporated to dryness. The residue was dissolved in 100 ml. of water, pH 10.1, the solution acidified to pH 5.0 with concentrated hydrochloric acid. The solution was diluted with 500 ml. of isopropyl alcohol added dropwise and the additional sodium chloride precipitate was filtered. The filtrate was concentrated to about 100 ml. and the insoluble product was filtered. There were obtained 37.1 g. of the product which melted at about 58° C. to about 68° C. On chilling the filtrate an additional 12.5 g. of the product were obtained.

Elemental analysis calculated for $C_6H_6N_2O_2$: Theory: C, 52.17; H, 4.38; N, 20.28; O, 23.17. Found: C, 51.92; H, 4.35; N, 19.98; O, 23.47.

B. Preparation of Title Compound

A solution of about 3 mmole of trimethylsilylated syn-7-[2-(2-aminothiazol-4-yl)-2-methoxyiminoacetamido]-3-iodomethyl-3-cephem-4-carboxylate in 8 ml. of acetonitrile was added to a solution of 415 mg. (3 mmole) of N-hydroxy 2-pyridinecarboxamide and 800 μl. of BSTFA in 5 ml. of acetonitrile and the mixture was stirred for one hour at room temperature. The mixture was diluted with 0.4 ml. of water and the product filtered. There were obtained 260 mg. of the crude product which was purified via HPLC.

EXAMPLE 7 syn-7-[2-(2-Aminothiazol-4-yl)-2-methoxyiminoacetamido]-3-[[4-(N-hydroxy-N-methylcarbamoyl)pyridinium]methyl]-3-cephem-4-carboxylate

A. Preparation of N-hydroxy-N-methyl 4-pyridinecarboxamide

A solution of 9.72 g. (180 mmole) of sodium methylate in 120 ml. of methyl alcohol is combined with a solution of 7.52 g. (90 mmole) of N-hydroxy methylamine hydrochloride in 120 ml. of methyl alcohol. To the combined solutions was added with stirring a solution of 12.37 g (90 mmole) of methyl 4-pyridinecarboxylate and the mixture was stirred at room temperature for five hours. The reaction mixture was filtered and the filtrate was evaporated under vacuum to a foam. The foam was stirred in 300 ml. of acetone and the insoluble material was filtered. The acetone insoluble material (17.28 g.) was stirred in 300 ml. of isopropyl alcohol and filtered. The filtrate was evaporated to dryness and the residue was stirred with 300 ml. of ethyl acetate. The insoluble crude product, 13.33 g., was boiled in 24 ml. of methyl alcohol:acetone, 1:1, v:v until solution was obtained. Acetone was added to the boiling solution to maintain volume. After solution was obtained the solution was stored in the freezer for 3 hours and filtered. There were obtained 3.77 g. of the product. A second crop of 1.46 g. was obtained on further chilling of the filtrate.

Both crops were combined and dissolved in 13 ml. of water, pH 11.0. The solution was acidified to pH 5.0 with 1 N hydrochloric acid and the product precipitated and was filtered. A second crop was obtained from the filtrate on further cooling.

The filtrate of the second crop material (1.46 g.) described above was treated in the same manner as described above for the solid product to provide additional purified product.

There were obtained 5.60 g. of purified N-hydroxy-N-methyl 4-pyridinecarboxamide.

Elemental analysis calculated for $C_7H_8N_2O_2$: Theory: C, 55.26; H, 5.30; N, 18.41; O, 21.03. Found: C, 55.37; H, 5.26; N, 18.21; O, 21.25.

Electrometric titration (water) pKa 3.55 and 7.90

B. Preparation of Title Compound

A suspension of 1.82 g. (4 mmole) of syn-7-[2-(2-aminothiaz-4-yl)-2-methoxyiminoacetamido]-3acetoxymethyl-3-cephem-4-carboxylic acid in 12 ml. of methylene chloride was treated with 1.13 g. (4.4 mmole) of BSTFA and the mixture stirred at 35° C. for 35 minutes. To the resultant solution of the trimethylsilylated derivative were added 2.40 g. (12 mmole) of TMSI and the mixture was stirred for 2 hours at room temperature. The reaction mixture was then evaporated to remove the solvent and the residue of product was dissolved in acetonitrile. The solution of the silylated 3-iodomethyl derivative was washed with hexane. To this solution was added a solution of 0.91 g. (6 mmole) of N-hydroxy-N-methyl 4-pyridinecarboxamide in 10 ml. of acetonitrile containing 1.54 g. (6 mmole) of BSTFA. The reaction mixture was stirred for 2.75 hours at room temperature and thereafter 0.59 ml. of water were added. The insoluble product was filtered and then triturated three times with 5 ml. of water each time. Each trituration was filtered and the filtrates combined and chromatographed over 125 g. of Sephadex G-10. Sixty fractions of 3.5 ml. volume were collected. Water was used as eluent. Each fraction was assayed by thin layer chromatography. Fractions 21-35 containing the product were combined and lyophilized. There were obtained 21 mg. of the product.

NMR (DMSO): signals at 3.30 (q, 2H), 3.34 (s, 3H), 3.79 (s, 3H), 5.15 (d, 1H), 5.43 (q, 2H), 5.75 (q, 1H), 6.74 (s, 1H), 7.21 (broad, 2H, exch.), 8.47 (d, 2H), 9.60 (d, 2H), and 9.63 (d, 1H, exch.) δ.

EXAMPLE 8 syn-7-[2-(2-Aminothiazol-4-yl)-2-methoxyiminoacetamido]-3-[[3-(N-hydroxy-N-methylcarbamoyl)pyridinium]methyl]-3-cephem-4-carboxylate A. Preparation of N-hydroxy-N-methyl 3-pyridinecarboxamide By following the reaction conditions and isolation procedures described by Example 7A, ethyl 3-pyridinecarboxylate was reacted with N-hydroxy methylamine. There were obtained 5.15 g. of the product.

B. Preparation of Title Compound

By following the reaction conditions and isolation procedures, the trimethylsilylated 3-iodomethyl derivative used in Example 7 is reacted with N-hydroxy-N-methyl 3-pyridinecarboxamide and the Title Compound is obtained.

EXAMPLE 9 syn-7-[2-(2-Aminothiazol-4-yl)-2-methoxyiminoacetamido]-3-[[2-(N-hydroxy-N-methylcarbamoyl)pyridinium]methyl]-3-cephem-4-carboxylate A. Preparation of N-hydroxy-N-methyl 2-pyridinecarboxamide By following the procedures and reaction conditions described by Example 7A, methyl 2-pyridinecarboxylate was reacted with N-hydroxy methylamine and N-hydroxy-N-methyl 2-pyridinecarboxamide was obtained.

B. Preparation of the Title Compound

In following the procedures and conditions described by Example 7B, bis-trimethylsilyl syn-7-[2-(2-aminothiazol-4-yl)-2-methoxyiminoacetamido]-3-iodomethyl-3-cephem-4-carboxylate is reacted with N-hydroxy-N-methyl 2-pyridinecarboxamide to provide the Title Compound.

EXAMPLE 10 syn-7-[2-(2-Aminothiazol-4-yl)-2-methoxyiminoacetamido]-3-[[4-(N-methoxycarbamoyl)-1-pyridinium]methyl]-3-cephem-4-carboxylate A. Preparation of N-methoxy 4-pyridinecarboxamide A solution of 16.20 g. (0.30 mmole) of sodium methylate in 240 ml. of methyl alcohol and a solution of 12.51 g. (0.15 mmole) of methoxyamine hydrochloride in 240 ml. of methyl alcohol were mixed at room temperature. To the white suspension which formed was added at room temperature over 20 minutes a solution of 20.61 g. (0.15 mmole) of methyl 4-pyridinecarboxylate in 120 ml. of methyl alcohol. The mixture was stirred at room temperature for 18 hours and then at the reflux temperature for 3.5 hours. After reflux the mixture was cooled to room temperature and filtered. The filtrate was evaporated to dryness and 100 ml. of water were added to the residue. The aqueous solution obtained was washed three times with 100 ml. portions of chloroform and the pH of the aqueous solution adjusted to 6.5 with concentrated hydrochloric acid. The acidic solution was evaporated to dryness and the residue was stirred with 250 ml. of THF and filtered. The filtrate was evaporated to dryness to yield 8.56 g. of N-methoxy 4-pyridinecarboxamide.

B. Preparation of Title Compound

The Title Compound is prepared by reacting bis-trimethylsilyl syn-7-[2-(aminothiazol-4-yl)-2-methoxyiminoacetamido]-3-iodomethyl-3-cephem-4-carboxylate with N-methoxy 4-pyridinecarboxamide.

We claim:

1. A compound of the formula

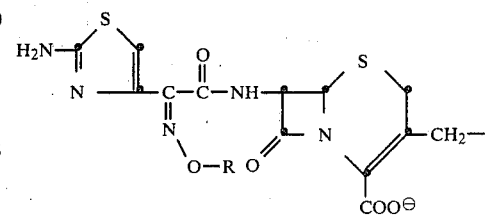

-continued

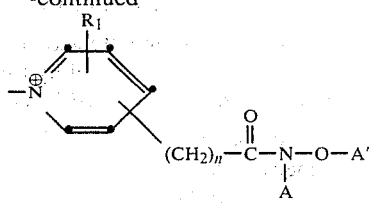

wherein R is C₁–C₄ alkyl or a group of the formula

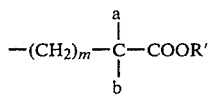

wherein m is 0, 1 or 2;
a and b independently are hydrogen or C₁–C₃ alkyl, or a and b taken together form a 3 to 6 membered carbocyclic ring; and R' is hydrogen or a carboxy protecting group;
R₁ is hydrogen or C₁–C₄ alkyl;
n is 0, or an integer from 1 to 3;

A and A' independently are hydrogen, allyl, or C₁–C₄ alkyl; and the pharmaceutically acceptable, non-toxic, salts thereof.

2. The compound of claim 1 wherein R is C₁–C₄ alkyl.
3. The compound of claim 2 wherein R₁ is hydrogen.
4. The compound of claim 3 wherein n is 0.
5. The compound of claim 4 wherein A and A' are hydrogen.
6. The compound of claim 5 of the formula

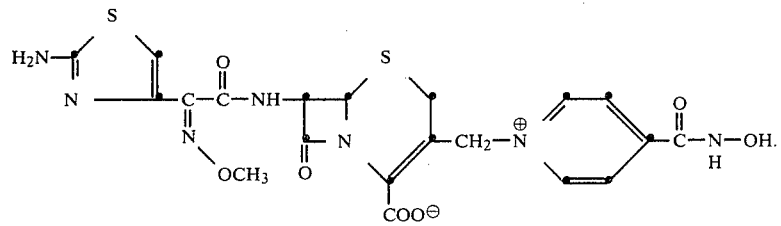

7. The compound of claim 5 of the formula

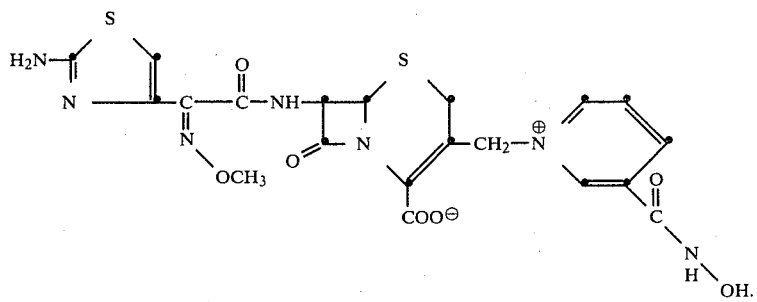

8. The compound of claim 5 of the formula

9. The compound of claim 4 wherein A' is hydrogen.
10. The compound of claim 9 of the formula

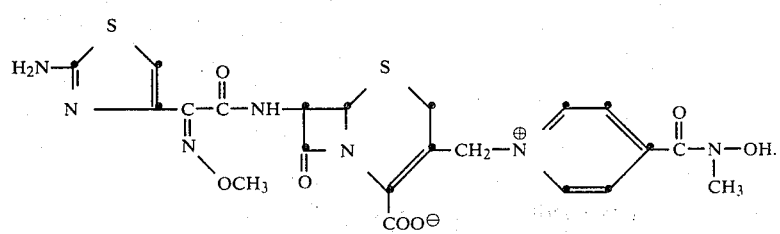

11. The compound of claim 9 of the formula

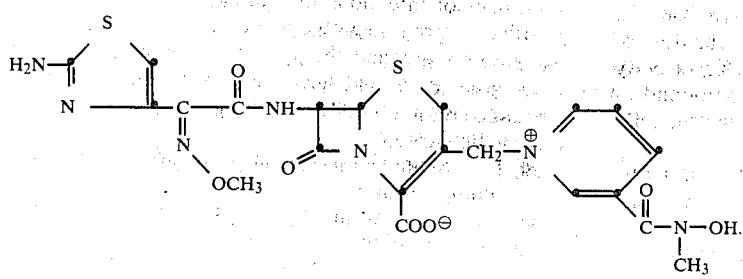

12. The compound of claim 9 of the formula

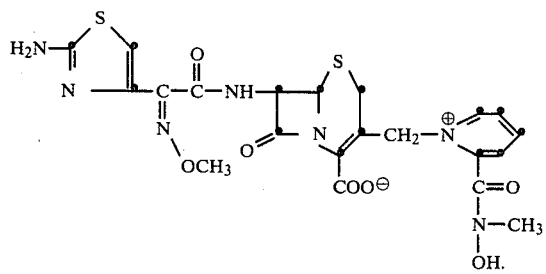

13. The compound of claim 3 wherein n is 1 or 2.
14. The compound of claim 13 wherein A and A' are hydrogen.
15. The compound of claim 14 of the formula

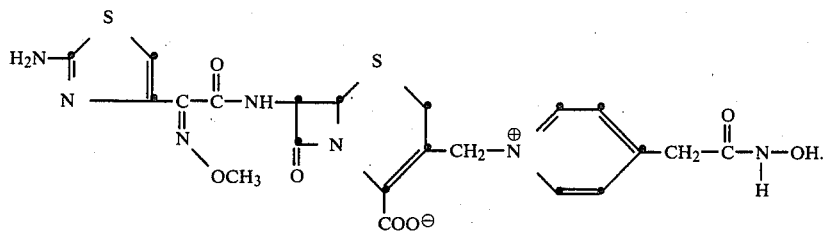

16. The compound of claim 14 of the formula

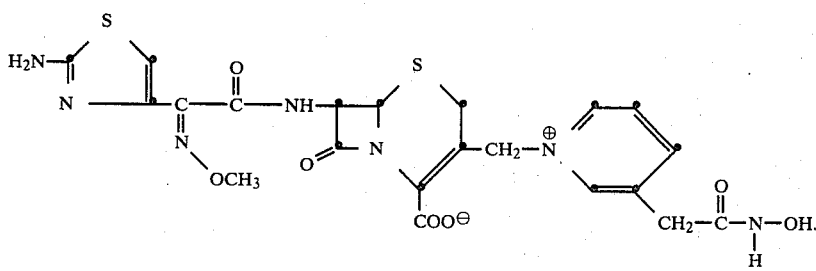

17. The compound of claim 14 of the formula

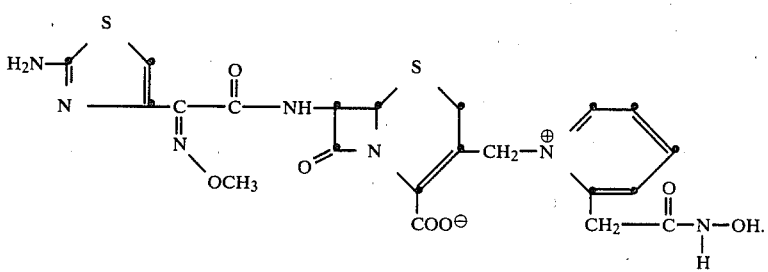

18. The compound of claim 3 wherein A' is $C_1$–$C_4$ alkyl and A is hydrogen or methyl.
19. The compound of claim 18 wherein A' is methyl.
20. The compound of claim 2 wherein $R_1$ is methyl, n is 0, and A and A' are hydrogen.
21. The compound of claim 1 wherein R is a group of the formula $$-(CH_2)_m-\underset{b}{\overset{a}{\underset{|}{\overset{|}{C}}}}-COOR'.$$

22. The compound of claim 21 wherein m is 0, a and b are both methyl and R' is hydrogen.
23. The compound of claim 22 wherein n is 0 and A and A' are both hydrogen.
24. The compound of claim 22 wherein n is 1 or 2 and A and A' are hydrogen or methyl.

25. The method for treating infections in a mammal caused by gram positive or gram negative bacteria which comprises administering parenterally at a dose of between about 25 mg/kg to about 500 mg/kg of body weight of said mammal of the antibiotic compound of claim 1, wherein R' is hydrogen, or a pharmaceutically acceptable, non-toxic salt thereof.

26. The method of claim 25 wherein the antibiotic compound R is $C_1$–$C_4$ alkyl, $R_1$ is hydrogen, and A and A' are both hydrogen or methyl.

27. The method of claim 26 wherein R is methyl, n is 0 and A and A' are both hydrogen.

28. A pharamceutical composition suitable for the treatment of infections in a mammal caused by gram positive or gram negative bacteria which comprises as the active ingredient the antibiotic compound of claim 1, wherein R' is hydrogen, or a pharmaceutically acceptable, non-toxic salt thereof, and a pharmaceutically acceptable carrier.

29. The composition of claim 28 suitable for intramuscular administration.

30. The composition of claim 28 suitable for intravenous administration.

* * * * *